(12) United States Patent
Yamamoto

(10) Patent No.: US 7,722,753 B2
(45) Date of Patent: May 25, 2010

(54) ELECTROPHORESIS PLATE

(75) Inventor: Rintaro Yamamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 903 days.

(21) Appl. No.: 11/360,676

(22) Filed: Feb. 24, 2006

(65) Prior Publication Data
US 2006/0191793 A1    Aug. 31, 2006

(30) Foreign Application Priority Data
Feb. 28, 2005  (JP) .............................. 2005-052440

(51) Int. Cl.
*G01N 27/453* (2006.01)
*B01D 57/02* (2006.01)

(52) U.S. Cl. ...................................... 204/600; 204/450
(58) Field of Classification Search ................ 204/450, 204/451, 455, 456, 466, 600; 422/100, 99, 422/58, 68.1
See application file for complete search history.

(56) References Cited
U.S. PATENT DOCUMENTS
5,560,811 A * 10/1996 Briggs et al. ................ 204/451
6,635,470 B1 * 10/2003 Vann ............................ 506/16
6,780,300 B1 * 8/2004 Alberto ....................... 204/601
2003/0156993 A1 * 8/2003 Staats .......................... 422/100

FOREIGN PATENT DOCUMENTS
JP  H11-502618    3/1999
JP  2001-517794   10/2001
JP  2002-207031   7/2002

* cited by examiner

*Primary Examiner*—Nam X Nguyen
*Assistant Examiner*—Gurpreet Kaur
(74) *Attorney, Agent, or Firm*—Manabu Kanesaka

(57) ABSTRACT

An electrophoresis plate has a plurality of separation channels provided inside a substrate. The separation channels are arranged along the surface of the substrate without intersecting each other, and the separation channels have openings on both ends on the substrate surface. When a voltage is applied between the two ends of the channel, a sample is separated by electrophoresis along the channel. The openings on one end are placed in a matrix pattern as sample inlet ports, and the pitch of that placement is set equal to the pitch of the wells of a sample plate containing the samples to be injected into the sample inlet ports. Since the pitch of the sample inlet ports pattern is equal to the pitch of the sample plate wells, sample injection can be performed quickly and conveniently even with a large number of separation channels.

9 Claims, 5 Drawing Sheets

ELECTROPHORESIS PLATE

BACKGROUND OF THE INVENTION AND RELATED ART STATEMENT

The present invention relates to an electrophoresis plate, which is used for separation by electrophoresis in fields such as biochemistry, molecular biology, and clinical practice, for example in DNA sequencing, for analyzing very minute quantities of proteins and amino acids, drugs, and the like, at high speed and with high resolution.

Electrophoresis devices have traditionally been used when analyzing very minute quantities of proteins and amino acids, and the like. There is a capillary electrophoresis device as a representative device, but it was complicated. Compensating for that drawback, an electrophoresis device having channels inside the substrate, aiming for acceleration of analysis and miniaturization of the device, is a so-called micro fluid device.

Prior electrophoresis methods using micro fluid devices are based on channels of cross injector design, having intersecting sample inlet channels in addition to separation channels (See Japanese Unexamined Patent Publication No. 2002-131279; Japanese Unexamined Patent Publication No. 2002-131280; Japanese Unexamined Patent Publication No. 2002-310990; and Japanese Unexamined Patent Publication No. 2003-166975).

However, with the cross injection method, there is a limit in the samples introduced into the separation channels due to the channel configuration, and it cannot handle diverse samples (for example, samples containing components having great differences of concentration).

Therefore, an electrophoresis plate having only separation channels in which the quantity of injected samples can be controlled by applied voltage and application time is used. That electrophoresis plate has plural separation channels inside the substrate, each of those separation channels consists of one channel, and voltage is applied between the two ends whereby the sample is separated by electrophoresis along the channel. Those separation channels are arranged along the surface of the substrate without intersecting each other, and in a manner so as to be collected from one end toward the other end, and they are made so as to avoid accumulation at the cathode end.

In the case of performing sample injection in the preprocessing process, from an MTP (Micro Type Plate) having 96 holes or 384 holes, which is commonly used as a sample plate, into an MEMS (Micro Electro Mechanical Systems) electrophoresis plate having a radial channel structure, because the pitch arrangement of the separation channels does not correspond to the pitch of the wells of the sample plate, injection of the samples on a one-by-one basis becomes necessary, and sample injection in a short time may become difficult.

An object of the present invention therefore is to provide an electrophoresis plate with which sample injection can be performed quickly and conveniently even when the number of separation channels is increased.

Further objects and advantages of the invention will be apparent from the following description of the invention.

SUMMARY OF THE INVENTION

The present invention is an electrophoresis plate, having plural separation channels provided inside a substrate, each of those separation channels consisting of one channel. When a voltage is applied between the two ends, a sample is separated by electrophoresis along the channel. The separation channels are arranged along the surface of the substrate without intersecting each other, and the separation channels have openings on both ends on the substrate surface. The openings on one end are placed in a matrix pattern as sample inlet ports, and the pitch of that placement is set equal to the pitch of the wells of the sample plate in which are contained the samples to be injected into the sample inlet ports.

The sample inlet ports placed in a matrix pattern must be made independent for each separation channel in order to prevent contamination by communication between adjacent inlet ports. However, in the case of forming sample inlet ports corresponding to the number of channels by adhering on resin or glass, poor adhesion to the substrate is not acceptable, and the electrophoresis plate becomes expensive.

Accordingly, in the present invention, the openings are formed on the glass substrate itself, and those openings are used as sample inlet ports (reservoirs).

If the openings are made, for example, as 384 holes (for example, a 16×24 arrangement), at most 15 channels must be cut between 4.5 mm openings.

However, if the channel width is about 100 µm, because the channel interval must be 300 µm or more considering the width necessary for glass bonding, with 15 channels a width of 4.3 mm (300 µm×14 channels+100 µm) becomes necessary. Furthermore, considering the necessary width between the openings and the ends of the channels, the width of the openings ends up being 200 µm or less. Considering the dispensing of samples, and furthermore, the injection of electrodes (0.5 mm) for injection, the width of the openings must be 1.5 mm or more.

Furthermore, in the event of sample injection, because contact between the electrode tip and the gel at the channel end completely obstructs injection of the sample, the separation channel between the opening and the channel end must be a distance of 1 mm or more.

In the case of forming by adhering the sample inlet ports on the glass substrate, the distance between the channel end and the electrode tip can be assured in a direction orthogonal to the channel. But, in the case of forming openings in the glass substrate as sample inlet ports, the distance must be worked in the channel direction, and openings having a width of 2 mm or more in the channel direction must be formed in the glass substrate. Here, although representative numbers are disclosed for purposes of explanation, the present invention is of course not limited to these numbers.

Therefore, in a preferred embodiment of the present invention, the shape of the inlet port is made as an elongated hole shape extending in the longitudinal direction of the channel.

In the case of the openings on the channel ends being placed in a matrix pattern with the same pitch arrangement as the wells of the sample plate, if the other ends of the channels are arranged in a straight line, a difference arises in the channel length according to the position of the opening. However, if the positions of the other ends are shifted in order to eliminate the unevenness of channel length, in the event of gel replacement for each phoresis, it becomes difficult to use the anode end as the gel injection port. This is because gel injection is performed with the other ends of the channels all together. In the case when the difference of channel lengths is great, the electric field strength becomes lower for longer channels during voltage application, and the degree of migration of the sample becomes lower. Also, by that the difference of phoresis times among channels becomes greater.

Because one of the characteristics of multi-electrophoresis is high throughput of analysis, the presence of channels having long phoresis times becomes a problem. Furthermore, for short channels having high electric field strength, because the speed of electrophoresis is fast, a problem arises that sufficient separation performance is not achieved.

Therefore, in another preferred embodiment of the present invention, the openings on the other ends of the separation channels are placed along a linear region in a direction nearly orthogonal to the longitudinal direction of the separation channels, and of the separation channels, the other ends of about half the number of separation channels, having the sample inlet ports placed nearer to the placement of the separation channels, are bent back and connected to the respective openings, whereby the difference of channel lengths among the separation channels is reduced.

In the electrophoresis plate of the present invention, by forming the openings on the glass substrate itself, the work of creation of sample inlet ports and adhesion using a separate member having plural holes opened is no longer necessary. Also, by the fact that the pitch of placement of the openings is equal to the pitch of the wells of the sample plate, moving the samples from the sample plate to the sample inlet ports and injection can be performed quickly and conveniently.

If the shape of the sample inlet port is made as an elongated hole shape extending in the longitudinal direction of the channel, it no longer contacts with adjacent openings in the direction orthogonal to the channel length, and more openings can be placed.

If the plate is made such that about half the number of the other ends of separation channels connected from the sample inlet ports are bent back and connected with the respective openings, the difference of channel lengths of the separation channels can be reduced. Thus, while realizing convenience of sample movement and injection, the accumulation of plural channels having stable phoresis among channels and having the same separation performance and phoresis time becomes possible in the case when the difference in the standard of the channel lengths is constrained.

DETAILED DESCRIPTION OF THE PREFERRED EMBODIMENTS

Figures 1A, 1B:
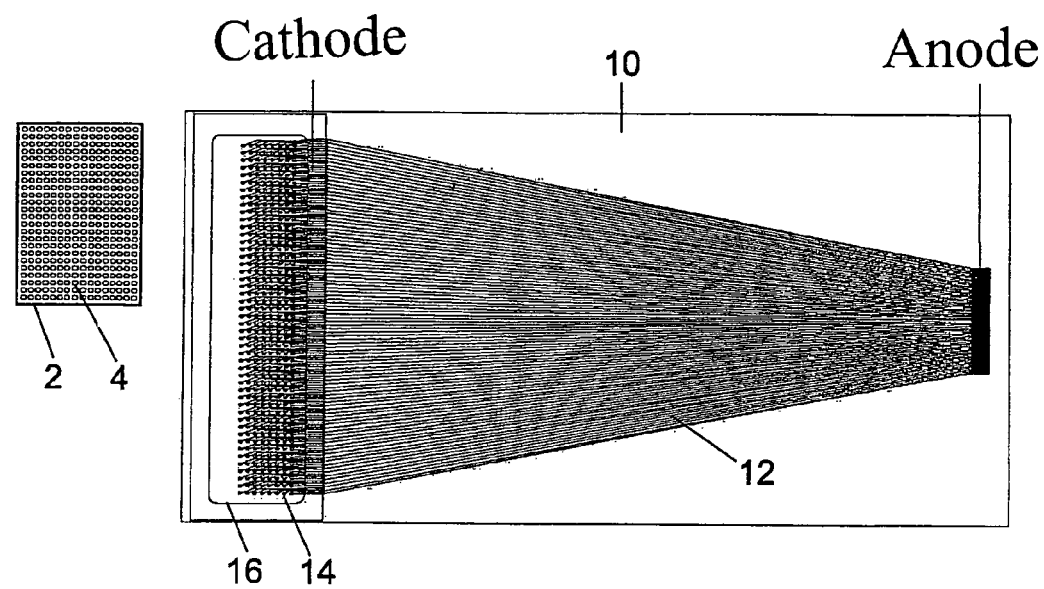
FIG. 1(A) is a plan view of a sample plate according to one embodiment of the present invention.
FIG. 1(B) is a perspective view of capillary channels in an electrophoresis member.

Below, one embodiment of the present invention, which uses an MEMS (Micro Electro Mechanical System) capillary plate as an electrophoresis member, is explained in detail while referring to the drawings.

Figures 1C, 1D:
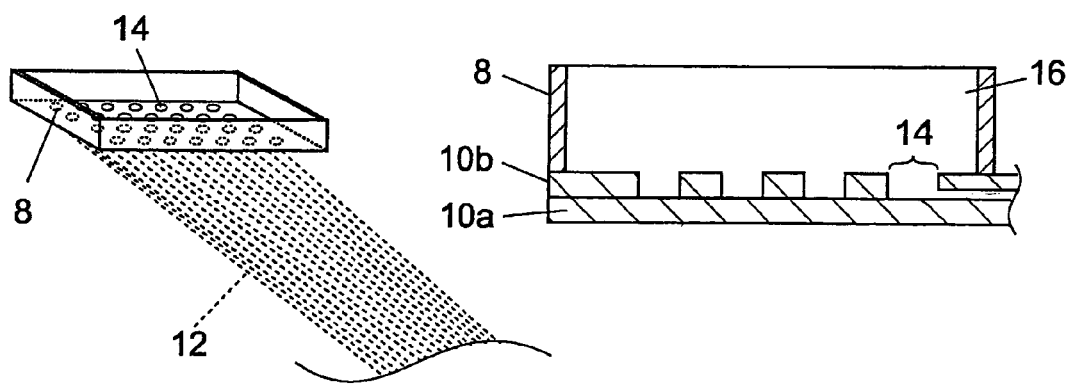
FIG. 1(C) is a perspective view of a cathode end of the electrophoresis member.
FIG. 1(D) is a sectional view of the cathode end of the electrophoresis member.
Figure 2A:
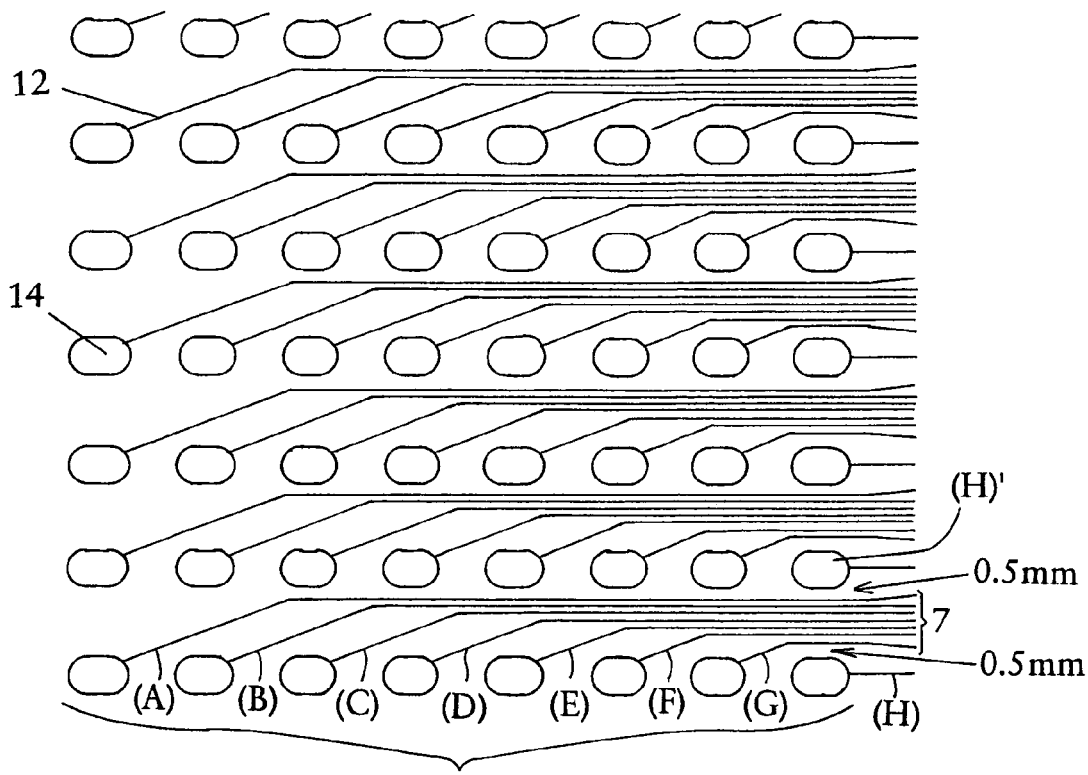
FIG. 2(A) is an enlarged plan view of the cathode end of the invention.
Figure 2B:
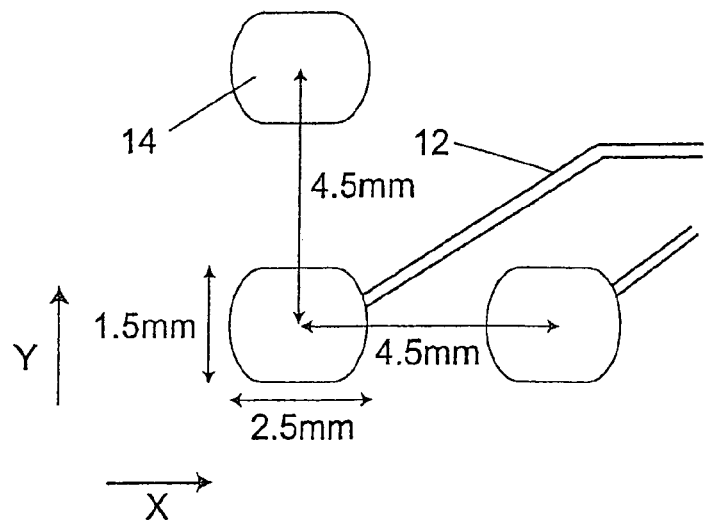
FIG. 2(B) is a further enlarged plan view showing reservoirs of the cathode end.
Figure 3:
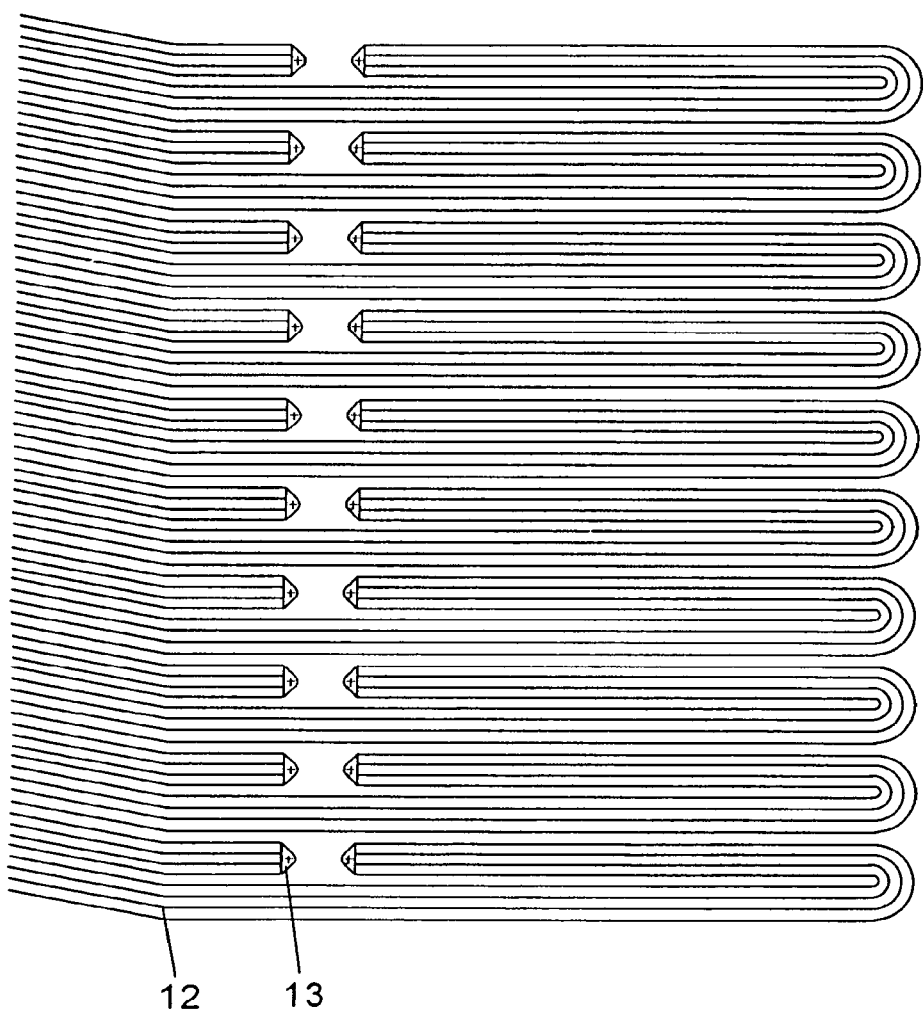
FIG. 3 is an enlarged plan view of an anode end of the electrophoresis member.

FIG. 1(A) is a typical drawing of a sample plate according to one embodiment of the present invention; FIG. 1(B) is a perspective view of capillary channels in an electrophoresis member; FIG. 1(C) is a perspective view of a cathode end of the electrophoresis member; and FIG. 1(D) is a sectional view of the cathode end of the electrophoresis member. FIG. 2(A) is an enlarged plan view of the cathode end, and FIG. 2(B) is a further enlarged plan view showing reservoirs of the cathode end. FIG. 3 is an enlarged plan view of an anode end of the electrophoresis member.

The electrophoresis plate 10 is a substrate made by bonding a pair of plate members 10a, 10b having a thickness of about 0.7 mm; one end is the cathode end, and the other end is the anode end. On the bonding surface side of one of the plate members 10a, plural, for example a total of 384, separation channels 12 consisting of capillary channels are formed and are arranged so as not to intersect with each other. On the other plate member 10b, through-holes 13, 14 are provided in positions on both ends of each separation channel 12.

The cathode end of each separation channel 12 is connected to a small-capacity reservoir 14 being a respective sample inlet port opened on the substrate surface, and on the substrate surface, a large-capacity reservoir 16 having a size encompassing all the small-capacity reservoirs 14 is formed being surrounded by a reservoir wall 8. The anode end of each separation channel 12 is opened so as to be connected to a common reservoir formed on the substrate surface.

As the material of the plate members 10a, 10b constituting the substrate, quartz glass, borosilicate glass, resin, and the like, can be used, and in the case when the components separated by electrophoresis are optically detected, a transparent material is selected. In the case of using a detecting means other than light, the material of the plate members 10a, 10b is not limited to a transparent one.

Formation of the separation channels 12 on the plate member 10a can be done by lithography or etching (wet etching or dry etching).

The width of the separation channel 12 is 100 nm-1000 μm, preferably 50-90 μm, and the depth is 100 nm-1000 μm, preferably 20-40 μm.

The small-capacity reservoir 14 is formed as a through-hole on the plate member 10b, its size is a diameter of 10 μm-3 mm, preferably 50 μm-2 mm, and it is set to a size suitable for injecting several 10 nL-several μL of sample. The through-holes on the plate member 10b can be formed by a method such as sand blasting or laser drilling.

Although wells 4 on sample plate 2 have 384 holes (a 16×24 arrangement), the small-capacity reservoirs 14 on the cathode end divide these into 192 holes each (an 8×24 arrangement), and are deployed (an 8×48 arrangement) in a direction orthogonal to the channels as shown in FIGS. 1(A)-(D) and 2(A),(B). The pitch of the openings in the X, Y directions is 4.5 mm, and the inlet ports have a size of 2.5 mm in the X direction and 1.5 mm in the Y direction.

If the number of inlet ports in the X direction is 8, the number of separation channels between the inlet ports in the Y direction is 7 as shown in FIG. 2(A). For example, in case the width of one separation channel is 100 μm and the space between two separation channels is 200 μm, as in the conventional channels, the width necessary for the separation channels from an upper edge of a top separation channel A to a lower edge of a bottom separation channel G becomes 1.9 mm (100 μm (separation channel)×7+200 μm (space between the separation channels)×6), so that the width necessary for well formation can be assured.

When further considering the necessary width of 1 mm (0.5 mm from the upper inlet port H' to the separation channel A, and 0.5 mm from the separation channel G to the inlet port of separation channel H), the inlet port having a size of 2.5 mm in the X direction and 1.5 mm in the Y direction can be employed.

In this case, for example, the difference between the maximum channel length and the minimum channel length becomes 31.5 mm.

FIG. 3 shows one embodiment having a placement such that, of the separation channels 12, half number (4) of the separation channels, having the sample inlet ports placed nearer to the anode end, are bent back in a U shape and are connected to the openings on the anode end.

On the anode end, the 384 channels are bundled for scanning by a fluorescence detector, their ends are bundled four channels each and are placed so that the terminals face each other, and they are connected to access holes 13 for gel filling and electrical communication.

The average length of the separation channels 12 in the above-described embodiment is 440 mm, the maximum channel length is 452.4 mm, and the minimum channel length is 430.8 mm. The difference of channel lengths in this case is 21.6 mm, and the percentage over the average channel length is 4.9%.

Next, the sample injection operation in the electrophoresis plate in FIGS. 1(A)-1(D) is explained.

(1) The electrophoresis plate 10 is kept in a 50° C. constant temperature state.

(2) The large-capacity reservoir 16 on the cathode side is filled with pure water, for example Milli-Q water being ultra-pure water, and all the separation channels 12 are filled with gel by pressurizing with a syringe from the anode side.

(3) Because the gel flowing out to the small-capacity reservoirs 14 from the separation channels 12 diffuses in the pure water in the large-capacity reservoir 16, the water and gel in the reservoirs 14, 16 is drawn by a suction nozzle, and the insides of the reservoirs 14, 16 are cleaned.

(4) After cleaning of the insides of the reservoirs 14, 16, the reservoir 16 on the cathode side and the reservoir on the anode side are filled with buffer solution, pre-separation is performed by applying voltage between the two reservoirs, and ions of impurities in the gel are moved to the anode or the cathode. The applied voltage, for example, is 125 V/cm, and the application time is 5 minutes.

(5) The buffer solution in the reservoir 16 on the cathode side is drawn, and the inside of the reservoir 16 is cleaned, and then the inside of the reservoir 16 is filled with pure water, for example Milli-Q water being ultra-pure water.

(6) After that, the samples are moved from the wells 4 of the sample plate 2 and injected into each small-capacity reservoir 14 of the reservoir 16 filled with pure water. Because the wells 4 of the sample plate 2 are 384 holes (16×24 arrangement), first the samples are moved from 192 holes (8×24 arrangement) being half, and then they are moved from 192 holes (8×24 arrangement) being the other half.

(7) The cathode is inserted into the small-capacity reservoir 14, and sample injection into the channel 12 is performed by applying voltage between the anode and the cathode. The applied voltage for sample injection, for example, is 50 V/cm, and the application time is 40 seconds.

(8) After cleaning by drawing the sample remaining inside the small-capacity reservoir 14 along with the pure water in the reservoir 16, the insides of the reservoirs 14, 16 are filled with buffer solution.

(9) The cathode is inserted into the reservoir 16, and electrophoresis separation and signal detection are performed by applying phoresis voltage between the cathode and the anode. For the applied voltage for phoresis separation, 70-300 V/cm is suitable, and for example, the applied voltage is 125 V/cm.

The anode may be provided in advance in each reservoir, or it may be inserted separately. Also, an electrode may be provided in advance in each reservoir 14 on the sample injection side, or it may be inserted separately.

FIGS. 4(A) to 4(H) show examples of a phoresis pattern produced with the above-described embodiment of the invention. Excited light is irradiated on a DNA sample separated by electrophoresis in the detection part, and its fluorescence is detected. The horizontal axis represents the scan number when scanned with the excited light, and it corresponds to the time. The vertical axis is the fluorescence strength.

FIGS. 4(A) to 4(H) are the results of fluorescence in eight channels arranged in sequence, and they are placed from nearest to the channel placement in the order from (A) to (H). That is, in FIG. 2(A), they are taken as (A)-(H) from the left in the drawing for a group of eight channels. Channels (A)-(D) are bent back on the anode side. Taking note of the peak around 20000 on the horizontal axis, it moves on toward the longer time side from FIGS. 4(A) to 4(D), and after once moving toward the shorter time side from FIGS. 4(D) to 4(E), it again moves toward the longer time side from FIGS. 4(E) to 4(H).

Figure 4A:
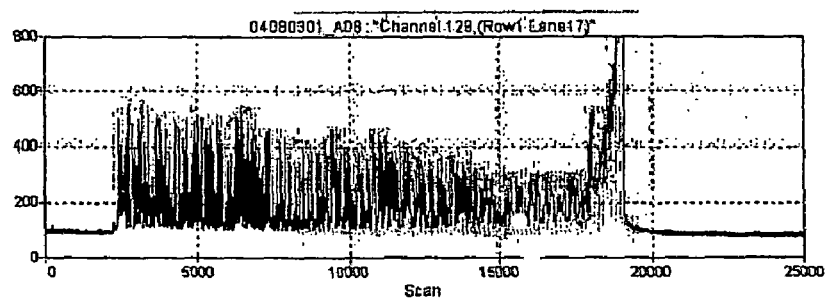
FIGS. 4(A) to 4(H) are graphs showing one example of a phoresis pattern.
Figure 4B:
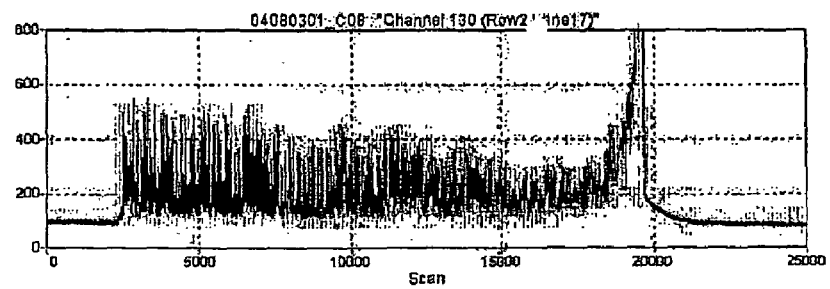
Figure 4C:
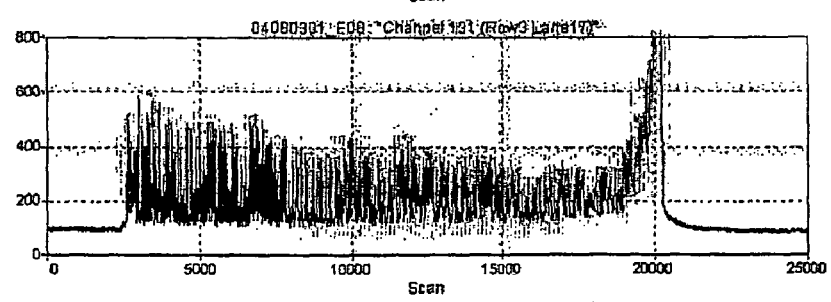
Figure 4D:
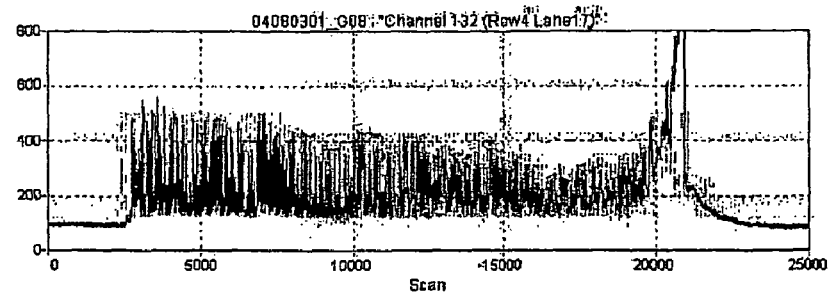
Figure 4E:
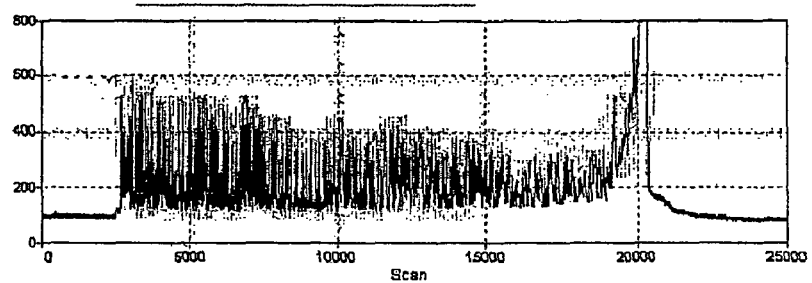
Figure 4F:
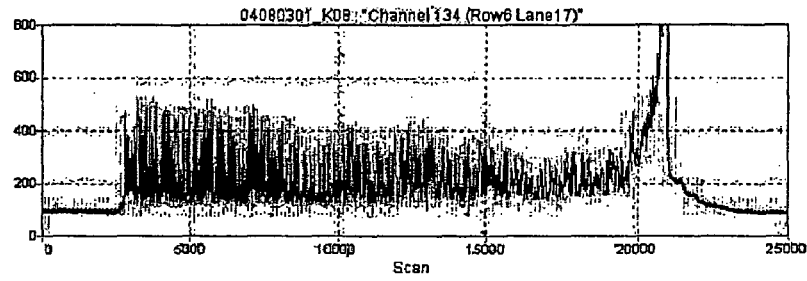
Figure 4G:
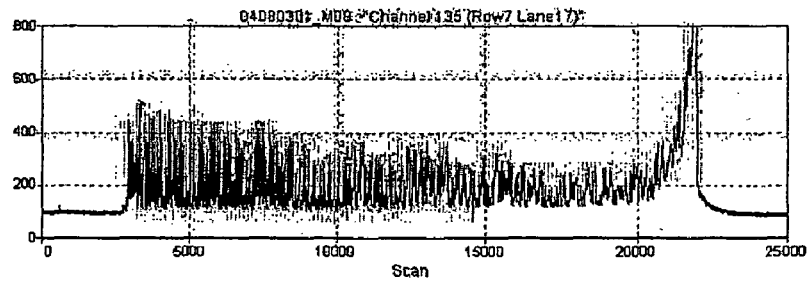
Figure 4H:
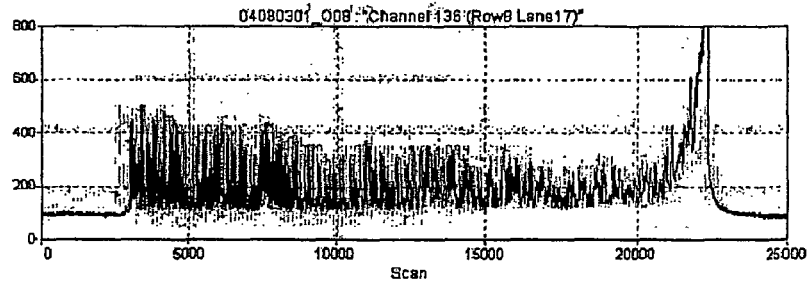

By bending back the four channels (A)-(D) of the eight channels, the difference of the positions of the peaks in FIG. 4(A) and FIG. 4(H) was reduced as shown in FIGS. 4(A)-(H).

The present invention is not limited only to the aforementioned embodiment. The invention can be implemented as long as about 50 μm can be assured for the channel width and about 2 mm in the X direction and 1.5 mm in the Y direction can be assured for the width for the reservoirs. Therefore, the inlet port on the cathode end is not limited to an elongated hole shape, and it also may be circular.

Also, the number of wells may be less than 384; for example, it may be 96. Also, the number of wells may be over 384; for example, as many as 1000 may be formed.

The invention can be used for separation by electrophoresis in fields such as biochemistry, molecular biology, clinical practice, for example in DNA sequencing, for analyzing very minute quantities of proteins and amino acids, drugs, and the like, at high speed and with high resolution.

The disclosure of Japanese Patent Application No. 2005-052440 filed on Feb. 28, 2005, is incorporated herein.

While the invention has been explained with reference to the specific embodiment of the invention, the explanation is illustrative, and the invention is limited only by the appended claims.

What is claimed is:

1. An electrophoresis plate for separating a sample, comprising:
   a substrate having a first end and a second end;
   a plurality of separation channels provided in the substrate as one group, each of the separation channels consisting of one channel, and arranged along a surface of the substrate without intersecting other separation channel;
   first separation channel openings provided at the respective separation channels on the first end of the substrate in a matrix pattern as sample inlet ports for receiving an injected sample from wells of a sample plate, the sample inlet ports having a pitch equal to a pitch of the sample plate wells;
   second separation channel openings provided at the separation channels in said one group on a side of the second end of the substrate along a linear region in a direction substantially orthogonal to a longitudinal direction of the separation channels; and
   bent portions provided at the second end and connected to approximately half of the separation channels in said one group, said half of the separation channels with the bent portions having their sample inlet ports located nearer to the second end, and connected to the second separation channel opening so as to reduce a difference of channel lengths relative to the separation channels without the bent portions in said one group.

2. The electrophoresis plate according to claim 1, wherein each of the sample inlet ports has an elongated hole shape extending in a longitudinal direction of the separation channel.

3. The electrophoresis plate according to claim 1, wherein each of the bent portions has a U shape.

4. The electrophoresis plate according to claim 1, wherein the sample inlet ports in one group are separated and spaced from a side of the first end to the side of the second end and arranged substantially linearly.

5. The electrophoresis plate according to claim 3, wherein the separation channels are arranged side by side and are sequentially connected to the sample inlet ports not to intersect with each other.

6. The electrophoresis plate according to claim 1, wherein the substrate comprises a pair of bonded plate members.

7. The electrophoresis plate according to claim 1, wherein the substrate further comprises a wall for surrounding the sample inlet ports to provide a material to the sample inlet ports at one time.

8. The electrophoresis plate according to claim 1, wherein two of the sample inlet ports adjacent to each other have an identical pitch therebetween.

9. The electrophoresis plate according to claim 1, wherein the sample inlet ports in said one group are arranged to be gradually spaced from a side of the first end to the side of the second end, and the approximately half of the separation channels having the bent portions in said one group have one common second separation channel opening facing another common second separation channel opening of the other half of the separation channels without the bent portions.

* * * * *